United States Patent
Chung et al.

(10) Patent No.: US 10,874,709 B2
(45) Date of Patent: Dec. 29, 2020

(54) CONJUGATE OF SALICYLIC ACID AND PEPTIDE

(71) Applicant: CAREGEN CO., LTD., Anyang-si (KR)

(72) Inventors: Yong Ji Chung, Seoul (KR); Eun Mi Kim, Yongin-si (KR)

(73) Assignee: CAREGEN CO., LTD., Anyang-Si (KR)

( * ) Notice: Subject to any disclaimer, the term of this patent is extended or adjusted under 35 U.S.C. 154(b) by 0 days.

(21) Appl. No.: 16/485,865

(22) PCT Filed: Feb. 16, 2017

(86) PCT No.: PCT/KR2017/001725
§ 371 (c)(1),
(2) Date: Aug. 14, 2019

(87) PCT Pub. No.: WO2018/151352
PCT Pub. Date: Aug. 23, 2018

(65) Prior Publication Data
US 2019/0374599 A1    Dec. 12, 2019

(51) Int. Cl.
| | | |
|---|---|---|
| *A61K 38/10* | (2006.01) | |
| *A61K 38/08* | (2019.01) | |
| *A61K 8/64* | (2006.01) | |
| *A61Q 19/00* | (2006.01) | |
| *C07K 7/06* | (2006.01) | |
| *A61K 8/368* | (2006.01) | |
| *A61K 31/60* | (2006.01) | |

(52) U.S. Cl.
CPC .............. *A61K 38/10* (2013.01); *A61K 8/368* (2013.01); *A61K 8/64* (2013.01); *A61K 31/60* (2013.01); *A61K 38/08* (2013.01); *A61Q 19/00* (2013.01)

(58) Field of Classification Search
CPC ........ A61K 31/60; A61K 38/08; A61K 38/10; A61K 45/06; A61K 8/368; A61K 8/64; A61Q 19/00; C07K 7/06
USPC ....................................................... 514/18.6
See application file for complete search history.

(56) References Cited

U.S. PATENT DOCUMENTS

| | | | | |
|---|---|---|---|---|
| 8,106,017 B2* | 1/2012 | Chung | ............. | C07K 14/57581 514/18.6 |
| 8,183,212 B2 | 5/2012 | Fujii et al. | | |
| 8,501,689 B2* | 8/2013 | Chung | ................. | C07K 14/475 514/21.6 |
| 8,729,028 B2* | 5/2014 | Chung | ................. | C07K 14/475 514/18.6 |
| 2011/0160131 A1 | 6/2011 | Chung et al. | | |

FOREIGN PATENT DOCUMENTS

| | | |
|---|---|---|
| EP | 2275440 A2 | 1/2011 |
| EP | 2383283 A2 | 11/2011 |
| EP | 2474555 A1 | 7/2012 |
| JP | 2009-512685 A | 3/2009 |
| JP | 2011-519358 A | 7/2011 |
| JP | 2012-515769 A | 7/2012 |
| JP | 2014-114291 A | 6/2014 |
| JP | 2016-222612 A | 12/2016 |
| KR | 20140107784 A | 9/2014 |
| KR | 20150011726 A | 2/2015 |
| WO | WO-2007/125619 A1 | 11/2007 |
| WO | WO-2009/125925 A2 | 10/2009 |

OTHER PUBLICATIONS

Nakamura et al., "A Novel Prodrug of Salicylic Acid, Salicylic Acid-Glutamic Acid Conjugate Utilizing Hydrolysis in Rabbit Intestinal Microorganisms," Chem. Pharm. Bull., 40(8): 2164-2168. (Year: 1992).*
Cao et al., "Propylene glycol-linked amino acid/dipeptide diester prodrugs of oleanolic acid for PepT1-mediated transport: synthesis, intestinal permeability, and pharmacokinetics," Mol Pharm. 10(4):1378-87 (2013).
Choi et al., "Solubility enhancement of salicylic acid by complexation with succinoglycan monomers isolated from Sinorhizobium meliloti," Bull Korean Chem Soc. 33(6):2091-4 (2012).
Golovanov et al., "A simple method for improving protein solubility and long-term stability," J Am Chem Soc. 126(29):8933-9 (2004).
International Search Report dated Nov. 15, 2017 for PCT International Application No. PCT/KR2017/001725, Chung et al., "Conjugate of Salicylic Acid and Peptide," filed Feb. 16, 2017 (7 pages).
Kato et al., "Mutational analysis of protein solubility enhancement using short peptide tags," Biopolymers. 85(1):12-8 (2006).
Nakamura et al., "A novel prodrug of salicylic acid, salicylic acid-glycylglycine conjugate, utilizing the hydrolysis in rabbit intestinal microorganisms," J. Pharm. Pharmacol. 44(9):713-716 (1992).
Notification of Reasons for Refusal dated Aug. 25, 2020 for Japanese Patent Application No. 2019-544021, Chung et al., "Conjugate of Salicylic Acid and Peptide," filed Feb. 16, 2017 (7 pages).
Sarigiannis et al., "Synthetic RGD peptides incorporating salicylic acid derivatives show antiplatelet activity *in vitro*," Peptides 2002, Proceedings of the Twenty-Seventh European Peptide Symposium, Aug. 31-Sep. 6, 2002, Sorrento, Italy, 606-607 (2002).

(Continued)

*Primary Examiner* — Julie Ha
(74) *Attorney, Agent, or Firm* — Clark & Elbing LLP; Susan M. Michaud

(57) ABSTRACT

An antibacterial, anti-inflammatory, or antioxidant composition and, more specifically, a compound having a structure in which salicylic acid is linked to a peptide via a covalent linkage, and an antibacterial, anti-inflammatory, or antioxidant pharmaceutical or cosmetic composition containing the compound, are described. The compound having a structure in which salicylic acid is linked to a peptide via a covalent linkage has excellent physiological activity, such as antibacterial, anti-inflammatory, or antioxidant activity, as well as excellent characteristics, such as solubility in water, and thus the compound can be favorably used in various fields of food, drug, or cosmetics.

13 Claims, 14 Drawing Sheets

Specification includes a Sequence Listing.

(56) References Cited

OTHER PUBLICATIONS

Suo et al, "Tandem heterocyclization activity of the multidomain 230 kDa HMWP2 subunit of Yersinia pestis yersiniabactin synthetase: interaction of the 1-1382 and 1383-2035 fragments," Biochemistry 38(42):14023-14035 (1999).
Eady et al., "The benefit of 2% salicylic acid lotion in acne—a placebo-controlled study," J. Dermatol. Treatment. 7:93-96 (1996).
Partial Supplementary European Search Report dated Oct. 15, 2020 for European Patent Application No. 17896681.8, Chung et al., "Conjugate of Salicylic Acid and Peptide," filed Feb. 16, 2017 (16 pages).
Zheng et al., "Clinical evidence on the efficacy and safety of an antioxidant optimized 1.5% salicylic acid (SA) cream in the treatment of facial acne: an open, baseline-controlled clinical study," Skin Res. Technol. 19(2):125-130 (2013).

* cited by examiner

CONJUGATE OF SALICYLIC ACID AND PEPTIDE

TECHNICAL FIELD

The present disclosure relates to a compound having a structure in which salicylic acid is linked to a peptide via a covalent bond, and use thereof.

SEQUENCE LISTING

The instant application contains a Sequence Listing which has been submitted electronically in ASCII format and is hereby incorporated by reference in its entirety. Said ASCII copy, created on Aug. 13, 2019 is named 51401_013001_Sequence_Listing_081319_ST25 and is 3,731 bytes in size.

BACKGROUND ART

Salicylic acid is a compound having a chemical formula of $C_7H_6O_3$ which corresponds to O-oxybenzoic acid. Since salicylic acid has various physiological activities such as antibacterial, anti-inflammatory, or antioxidant activity as well as antipyretic or analgesic activity, it is widely used in foods, drugs, cosmetics, etc. For example, salicylic acid is used as an exfoliating agent, a hair-conditioning agent, an anti-dandruff agent, or a skin-conditioning agent in cosmetic formulations, and salicylic acid derivatives are known to be used as preservatives, UV absorbers, fragrances, solvents, etc. in cosmetics (Korean Patent Publication No. 10-2009-0004980). Further, salicylic acid and derivatives thereof have biological effects on the skin, and specifically, have been used to improve major clinical symptoms of skin aging such as fine lines and wrinkles, breakdown of skin tissue, changes in skin color, and loss of skin firmness and tension (Korean Patent Publication No. 10-2000-0017297).

However, use of salicylic acid and derivatives thereof may cause tingling, itching, and tightness which cause considerable discomfort, after application to the skin, and thus users with sensitive skin often suffer damage when they use such compounds. In addition, since salicylic acid has very low solubility in water, it is necessary to add various organic solvents in order to solubilize it, which may make compositions containing salicylic acid more inconvenient.

Accordingly, there is a need to develop a novel compound which may improve the problems of salicylic acid, specifically, low solubility in water, and may further enhance physiological efficacy of salicylic acid.

DESCRIPTION OF EMBODIMENTS

Technical Problem

To improve the existing problems of salicylic acid, an object of the present disclosure is to provide a substance having excellent characteristics, such as solubility in water, while having physiological activity equivalent to or superior to that of a natural form of salicylic acid.

Solution to Problem

To achieve the above object, the present disclosure provides a compound having a structure in which salicylic acid is linked to a peptide via a covalent linkage.

According to one embodiment of the present disclosure, the peptide may consist of 2 to 30 amino acid sequences, 5 to 20 amino acid sequences, 8 to 15 amino acid sequences, or 10 to 12 amino acid sequences, but is not limited thereto.

According to another embodiment of the present disclosure, the peptide may be a water-soluble peptide, but is not limited thereto. According to an embodiment of the present disclosure, in the water-soluble peptide, a proportion of amino acids having hydrophilic side chains may be as high as 50% or more, 60% or more, 70% or more, 80% or more, 90% or more, or 100%. According to another embodiment of the present disclosure, in the water-soluble peptide, the number of amino acids having hydrophobic side chains may be five or less, four or less, three or less, two or less, or one, or none.

According to still another embodiment of the present disclosure, the peptide may be a peptide consisting of an amino acid sequence of SEQ ID NO: 1 to SEQ ID NO: 4, but is not limited thereto.

Further, the present disclosure provides an antibacterial, anti-inflammatory, or antioxidant pharmaceutical composition, the composition including any one of the compounds described above.

Further, the present disclosure provides an antibacterial, anti-inflammatory, or antioxidant cosmetic composition, the composition including any one of the compounds described above.

According to one embodiment of the present disclosure, the cosmetic composition may have a formulation such as a softener, a nourishing toner, a nutrient cream, a massage cream, an essence, an eye cream, a cleansing cream, a cleansing foam, a cleansing water, a facial mask, a spray, a powder, a hair tonic, a hair cream, a hair lotion, a hair shampoo, a hair rinse, a hair conditioner, a hair spray, a hair aerosol, a pomade, a sol gel, an emulsion, an oil, a wax, or an aerosol, but is not limited thereto.

Advantageous Effects of Disclosure

A compound having a structure, in which salicylic acid is linked to a peptide via a covalent linkage, of the present disclosure has excellent physiological activity, such as antibacterial, anti-inflammatory, or antioxidant activity, as well as excellent characteristics, such as solubility in water, and thus the compound may be usefully applied to various fields of foods, drugs, cosmetics, etc.

BEST MODE

To achieve the above objects, the present disclosure provides a compound having a structure, in which salicylic acid is linked to a peptide via a covalent linkage.

The salicylic acid may be 2-hydroxybenzoic acid having a chemical formula of $C_7H_6O_3$, and may have a chemical structure represented by the following formula.

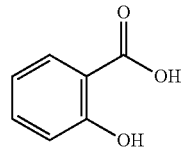

In the present disclosure, the term "peptide" means a linear molecule formed by amino acid residues which are linked to each other via a peptide bond. The peptide may be prepared according to a common biological or chemical synthesis method known in the art, specifically, solid-phase synthesis techniques (Merrifield, J. Amer. Chem. Soc. 85:2149-54(1963); Stewart, et al., Solid Phase Peptide Synthesis, 2nd. ed., Pierce Chem. Co.: Rockford, 111(1984)).

The peptide may be to enhance solubility of salicylic acid, and in this regard, the peptide may be a water-soluble peptide, but is not limited thereto. According to one embodiment of the present disclosure, the peptide may consist of 2 to 30 amino acid sequences, 5 to 20 amino acid sequences, 8 to 15 amino acid sequences, or 10 to 12 amino acid sequences. According to an embodiment of the present disclosure, in the peptide, a proportion of amino acids having hydrophilic side chains may be as high as 50% or more, 60% or more, 70% or more, 80% or more, 90% or more, or 100%. According to another embodiment of the present disclosure, in the peptide, a proportion of amino acids having hydrophobic side chains may be as low as less than 50%, 40% or less, 30% or less, 20% or less, 10% or less, or 0%. As used herein, the "amino acids having hydrophilic side chains" represent arginine (Arg), histidine (His), lysine (Lys), aspartic acid (Asp), glutamic acid (Glu), serine (Ser), threonine (Thr), asparagine (Asn), glutamine (Gln), cysteine (Cys), selenocysteine (Sec), glycine (Gly), and proline (Pro), and the "amino acids having hydrophobic side chains" represent alanine (Ala), valine (Val), isoleucine (Ile), leucine (Leu), methionine (Met), phenylalanine (Phe), tyrosine (Tyr), and tryptophan (Trp), but are not limited thereto. In addition to the above-mentioned amino acids which exist in nature, variants thereof, etc. may be used without limitation. According to an embodiment of the present disclosure, in the peptide, the number of amino acids having hydrophobic side chains may be five or less, four or less, three or less, two or less, or one, or may be none. According to an embodiment of the present disclosure, the peptide may be a peptide consisting of an amino acid sequence of SEQ ID NO: 1 to SEQ ID NO: 4, but is not limited thereto.

Figure 1:
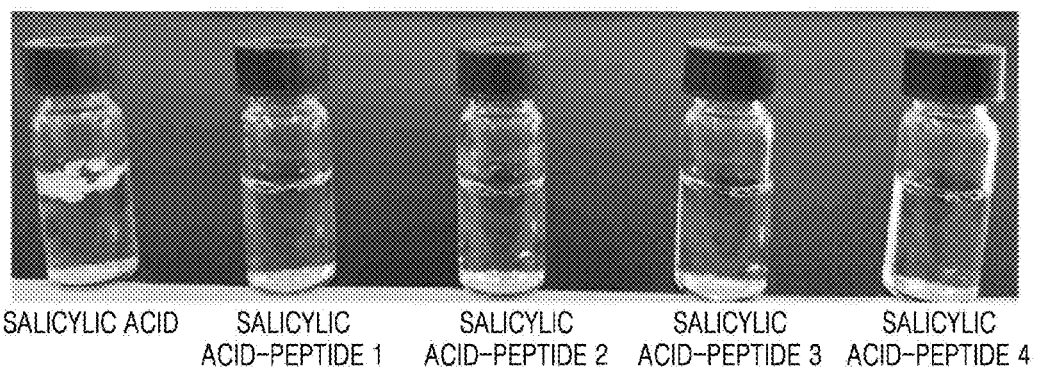
FIG. 1 shows an image showing solubility of compounds of the present disclosure and salicylic acid in water.
Figure 2A:
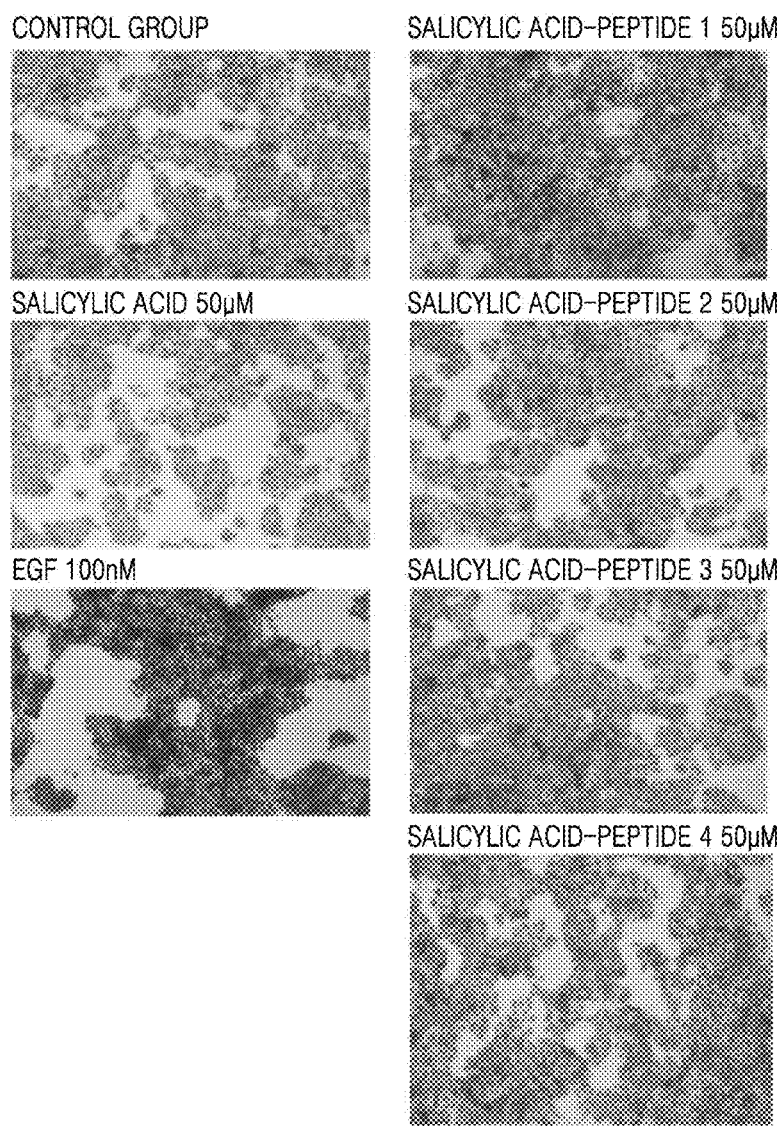
FIG. 2A shows immunostaining images showing the morphology and the number of keratinocytes after treatment with the compounds of the present disclosure and salicylic acid, respectively.
Figure 2B:
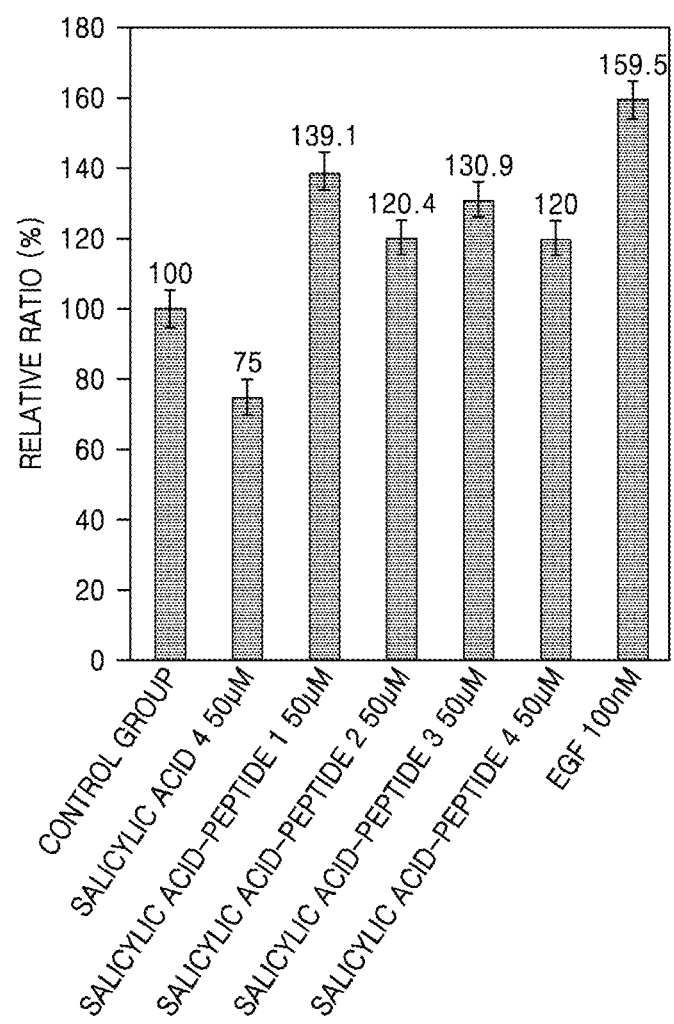
FIG. 2B is a graph showing the relative number of keratinocytes according to treatment concentrations of the compounds.

According to an embodiment of the present disclosure, the compound of the present disclosure may have excellent solubility in water (see FIG. 1B), and may also have a keratinocyte growth-stimulating ability (see FIGS. 2A and 2B). According to another embodiment of the present disclosure, the compound of the present disclosure may have antibacterial activity against *Propionibacterium acnes* (see FIGS. 3A and 3B), and antioxidant activity on various cell lines (see FIGS. 4A to 6B). According to still another embodiment of the present disclosure, the compound of the present disclosure may increase expression of extracellular matrix secreted from cells (see FIGS. 7A and 7B), and may have inhibitory activity on *Propionibacterium acnes*-induced inflammatory cytokine expression (see FIG. 8).

The compound of the present disclosure as it is may be very stable, but its stability may be further improved by modifying any amino acid constituting the peptide linked to the compound. According to one embodiment of the present disclosure, the N-terminus of the peptide may be bound with a protecting group selected from the group consisting of an acetyl group, a fluorenyl methoxy carbonyl group, a formyl group, a palmitoyl group, a myristyl group, a stearyl group, and polyethylene glycol (PEG), thereby further improving the stability. According to another embodiment of the present disclosure, the peptide may be bound with a protecting group selected from the group consisting of an acetyl group, a fluorenyl methoxy carbonyl group, a formyl group, a palmitoyl group, a myristyl group, a stearyl group, and polyethylene glycol (PEG), thereby further improving the stability.

The above-described amino acid modification may function to greatly improve stability of the compound of the present disclosure. As used herein, the term "stability" is used to include the meaning of "in vitro" stability such as storage stability (e.g., room-temperature storage stability) as well as "in vivo" stability. Further, the above-described protecting group may serve to protect the compound of the present disclosure from attack of proteases in vivo and in vitro.

Further, the present disclosure provides an antibacterial, anti-inflammatory, or antioxidant composition including the compound as an active ingredient. According to still another aspect of the present disclosure, the present disclosure provides a composition for improving skin conditions, the composition including the compound as an active ingredient. In the present disclosure, the composition may be in the form of a pharmaceutical composition, a health food, or a cosmetic composition, but is not limited thereto. Further, according to an embodiment of the present disclosure, the improvement of skin conditions by the compound of the present disclosure may include wrinkle improvement, skin elasticity improvement, skin aging prevention, skin moisturizing improvement, wound repair, or skin regeneration, but is not limited thereto.

Since the composition of the present disclosure includes the above-described compound of the present disclosure as an active ingredient, descriptions common to the two are omitted to avoid the excessive complexity of the present disclosure.

According to an embodiment of the present disclosure, the composition of the present disclosure is a pharmaceutical composition including (a) a pharmaceutically effective amount of the above-described compound of the present disclosure; and (b) a pharmaceutically acceptable carrier.

In the present disclosure, the term "pharmaceutically effective amount" means an amount which is sufficient to achieve the above-described efficacy or activity of the compound of the present disclosure.

The pharmaceutically acceptable carrier included in the pharmaceutical composition of the present disclosure may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, etc. which are commonly used upon formulating, but is not limited thereto. The pharmaceutical composition of the present disclosure may further include a lubricant, a wetting agent, a sweetener, a flavor, an emulsifier, a suspending agent, a preservative, etc., in addition to the above ingredients. An appropriate pharmaceutically acceptable carrier and formulation are described in detail in Remington's Pharmaceutical Sciences (19th ed., 1995).

The pharmaceutical composition of the present disclosure may be formulated in a unit dosage form or into a multidose container using a pharmaceutically acceptable carrier and/or excipient according to a method that may be easily carried out by those skilled in the art to which the present disclosure pertains. In this regard, the formulation may be in the form of a solution, a suspension, or an emulsion in an oily or aqueous medium, or in the form of an extract, a powder, granules, a tablet, a capsule, or a gel (e.g., a hydrogel), and may further include a dispersing agent or a stabilizing agent.

The pharmaceutical composition according to the present disclosure may be administered orally or parenterally at the time of clinical administration, and may be used in the form of a general pharmaceutical preparation. That is, the pharmaceutical composition of the present disclosure may be administered in various forms for oral and parenteral administration at the time of practical clinical administration. The formulation may be prepared using a commonly used diluent or excipient, such as a filler, an extender, a binder, a wetting agent, a disintegrant, a surfactant, etc. Solid formulations for oral administration may include a tablet, a pill, a powder, granules, a capsule, etc., and these solid formulations may be prepared by mixing an herbal extract or a herbal fermented product with at least one excipient, for example, starch, calcium carbonate, sucrose, lactose, gelatin, etc. In addition to the excipient, a lubricant such as magnesium stearate, talc, etc. may also be used. Liquid formulations for oral administration may include a suspension, a liquid formulation for internal use, an emulsion, a syrup, etc. In addition to a commonly used diluent such as water and liquid paraffin, various excipients, for example, a wetting agent, a sweetener, an aromatic, a preservative, etc. may also be included. Formulations for parenteral administration may include a sterilized aqueous solution, a non-aqueous solvent, a suspension, an emulsion, a lyophilized formulation, and a suppository. The non-aqueous solvent or suspension may include propylene glycol, polyethylene glycol, vegetable oil such as olive oil, injectable ester such as ethyl oleate, etc. As a base of the suppository, witepsol, macrogol, tween 61, cocoa butter, laurin butter, glycerol, gelatin, etc. may be used.

Dosage units may contain, for example, 1, 2, 3, or 4 single doses, or one-half, one-third, or one-fourth of a single dose. A single dose contains an amount of the active drug administered once, and generally corresponds to a whole, half, third, or quarter of the daily dosage.

The pharmaceutical composition of the present disclosure may be formulated in a unit dosage form or into a multidose container using a pharmaceutically acceptable carrier and/or excipient according to a method that may be easily carried out by those skilled in the art to which the present disclosure pertains. In this regard, the formulation may be in the form of a solution, a suspension, or an emulsion in an oily or aqueous medium, or in the form of an extract, a powder, granules, a tablet, a capsule, or a gel (e.g., a hydrogel), and may further include a dispersing agent or a stabilizing agent.

According to an embodiment of the present disclosure, the composition of the present disclosure may be a cosmetic composition including (a) a cosmetically effective amount of the above-described compound of the present disclosure; and (b) a cosmetically acceptable carrier.

In the present disclosure, the term "cosmetically effective amount" means an amount which is sufficient to achieve the above-described skin-improving efficacy of the compound of the present disclosure.

The cosmetic composition of the present disclosure may be prepared into any formulation common in the art, and for example, prepared into a solution, a suspension, an emulsion, a paste, a gel, a cream, a lotion, a powder, a soap, a surfactant-containing cleanser, an oil, a powder foundation, an emulsion foundation, a wax foundation, a spray, etc., but is not limited thereto. More specifically, the cosmetic composition may be prepared into various formulations such as a softener, a nourishing toner, a nutrient cream, a massage cream, an essence, an eye cream, a cleansing cream, a cleansing foam, a cleansing water, a facial mask, a spray, a powder, a hair tonic, a hair cream, a hair lotion, a hair shampoo, a hair rinse, a hair conditioner, a hair spray, a hair aerosol, a pomade, a solution such as a gel, a sol gel, an emulsion, an oil, a wax, an aerosol, etc., but is not limited thereto.

When the formulation of the present disclosure is a paste, a cream, or a gel, an animal oil, a plant oil, wax, paraffin, starch, tragacanth, cellulose derivatives, polyethylene glycol, silicone, bentonite, silica, talc, zinc oxide, etc. may be used as a carrier component.

When the formulation of the present disclosure is a powder or a spray, lactose, talc, silica, aluminum hydroxide, calcium silicate, or polyamide powder may be used as a carrier component. In particular, when the formulation of the present disclosure is a spray, it may further include a propellant such as chlorofluorohydrocarbon, propane/butane, or dimethyl ether, but is not limited thereto.

When the formulation of the present disclosure is a solution or an emulsion, a solvent, a solubilizer or an emulsifier may be used as a carrier component. For example, water, ethanol, isoproanol, ethyl carbonate, ethyl acetate, benzyl alcohol, benzyl benzoate, propylene glycol, 1,3-butylglycol oil, glycerol fatty ester, or fatty acid ester of polyethylene glycol or sorbitan may be used, but is not limited thereto.

When the formulation of the present disclosure is a suspension, a liquid diluent such as water, ethanol, or propylene glycol; a suspending agent such as ethoxylated isostearyl alcohol, polyoxyethylene sorbitol ester, and polyoxyethylene sorbitan ester; microcrystalline cellulose; aluminum metahydroxide; bentonite; agar; tragacanth, etc. may be used as a carrier component, but is not limited thereto.

When the formulation of the present disclosure is a surfactant-containing cleanser, aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives, ethoxylated glycerol fatty acid ester, etc. may be used as a carrier component, but is not limited thereto.

When the formulation of the present disclosure is a hair shampoo, the compound of the present disclosure may be mixed with base components for shampoo, such as a thickener, a surfactant, a viscosity adjuster, a moisturizer, a pH adjuster, a preservative, an essential oil, etc. As the thickener, CDE may be used. As the surfactant, LES which is an anionic surfactant and coco betaine which is an amphoteric surfactant may be used. As the viscosity adjuster, polyquater may be used. As the moisturizer, glycerin may be used. As the pH adjuster, citric acid or sodium hydroxide may be used. As the preservative, a grapefruit extract may be used. In addition, essential oils (e.g., cedarwood, peppermint, rosemary, etc.), silk amino acids, panthenol, and vitamin E may be added. According to an embodiment of the present disclosure, when the compound of the present disclosure is regarded as 100 parts by weight, 5 to 10 parts by weight of CDE; 30 to 40 parts by weight of LES; 10 to 20 parts by weight of coco betaine; 0.1 to 0.2 parts by weight of polyquater; 5 to 10 parts by weight of glycerin; 0.1 to 1.01 parts by weight of grapefruit extract; 0.5 to 1 part by weight of silk amino acid; 0.5 to 1 part by weight of panthenol; 0.5 to 2 parts by weight of vitamin E; and 0.01 to 0.1 part by weight of at least one of cedarwood, peppermint, and rosemary as the essential oil may be mixed, but is not limited thereto.

The components included in the cosmetic composition of the present disclosure may include components commonly used in cosmetic compositions, in addition to the compound of the present disclosure as an active ingredient and the carrier component, and may include, for example, common additives such as an antioxidant, a stabilizer, a solubilizer, a vitamin, a pigment, and a fragrance, but is not limited thereto.

Hereinafter, the present disclosure will be described in detail with reference to Examples.

However, these Examples are for illustrative purposes only, and the content of the present disclosure is not intended to be limited by the following Examples.

Example 1. Synthesis of Compounds of the Present Disclosure

<1-1> Synthesis of Peptides
<1-1-1> Synthesis of Peptide of SEQ ID NO: 1

700 mg of chlorotrityl chloride resin (CTL resin, Nova biochem [0064] Cat No. 01-64-0021) was added to a reactor, and 10 ml of methylene chloride (MC) was added thereto, followed by stirring for 3 minutes. The solution was removed, and 10 ml of dimethytformamide (DMF) was added, and stirred for 3 minutes to remove the solvent. 10 ml of a dichloromethane solution was added to the reactor, and 200 mmole of Fmoc-His(Trt)-OH (Bachem, Swiss) and 400 mmole of diisopropylethylamine (DIEA) were added thereto, and dissolved well by stirring, and allowed to react under stirring for 1 hour. After reaction, washing was carried out, and methanol and DIEA (2:1) were dissolved in dichloromethane (DCM) and allowed to react for 10 minutes, followed by washing with an excessive amount of DCM/DMF (1:1). The solution was removed, 10 ml of DMF was added, and stirred for 3 minutes. Then, the solvent was removed again. 10 ml of a deprotecting solution (20% piperidine/DMF) was added to the reactor, and stirred at room temperature for 10 minutes. Then, the solution was removed. The equivalent amount of the deprotecting solution was added, and allowed to react for 10 minutes. Then, the solution was removed, and washing was carried out with DMF twice, with MC once, and with DMF once each for 3 minutes. Thus, a His(Trt)-CTL resin was prepared.

10 ml of DMF solution was added to a new reactor, and 200 mmole of Fmoc-Thr(tBu)-OH(Bachem, Swiss), 200 mmole of HoBt, and 200 mmole of Bop were added and dissolved well by stirring. 400 mmole of DIEA was added in two fractions to the reactor, and stirred for at least 5 minutes until all solids were dissolved. The mixed solution in which the amino acids were dissolved was added to the reactor containing the deprotected resin, and allowed to react at room temperature for 1 hour under stirring. The reaction solution was removed, and stirring was performed with DMF solution three times each for 5 minutes, followed by removing. A small amount of the reaction resin was taken, and reactivity thereof was examined by a Kaiser test (a ninhydrin Test). Deprotection reaction was allowed twice using the deprotecting solution in the same manner as above to prepare a Thr(tBu)-His(Trt)-CTL resin. Sufficient washing was carried out with DMF and MC, and the Kaiser test was further performed. Then, the following amino acid attachment test was performed in the same manner as above.

In accordance with the selected amino acid sequence, Fmoc-Trp, Fmoc-Gly, Fmoc(Gly), Fmoc-Lys(Boc), Fmoc-Lys(Boc), Fmoc-Ser(tBu), Fmoc-Lys(Boc), and Fmoc-Tyr(tBu) were serially reacted in this order. Fmoc-protecting group was reacted with the deprotecting solution twice each for 10 minutes, and then washed well and removed. Acetic anhydride and DIEA, HoBt were added and allowed to acetylate for 1 hour, and then the prepared peptidyl resin was washed with DMF, MC, and methanol each three times, and nitrogen gas was slowly applied to dry the resin. Then, the resin was completely dried under vacuum in the presence of $P_2O_5$. 30 ml of a leaving solution [95% trifluoroacetic acid, 2.5% distilled water, and 2.5% thioanisole] was added, and then reacted at room temperature for 2 hours with intermittent agitating. The resin was filtered, and washed with a small amount of TFA solution, after which the filtrate was combined with the mother liquor. After distillation under reduced pressure to reduce the total volume by half, precipitation was induced using 50 ml of cold ether, and the formed precipitate was collected by centrifugation, followed by washing twice with cold ether. After removing the mother liquor, the resultant was sufficiently dried under nitrogen atmosphere to synthesize 1.15 g of unpurified Ac-YK-SKKGGWTH peptide (SEQ ID NO: 1) (yield 89.5%). A molecular weight thereof was measured as 1233.3 (a theoretical value: 1233.4) by a molecular weight analyzer.

<1-1-2> Synthesis of Peptides of SEQ ID NO: 2 to SEQ ID NO: 4

A peptide of SEQ ID NO: 2 (Tyr-Ile-Ser-Lys-Lys-His-Ala-Gly-Lys-Asn-Trp-Phe: YISKKHAGKNWF), a peptide of SEQ ID NO: 3 (Lys-Leu-Lys-Lys-Thr-Glu-Thr-Gln: KLKKTETQ), and a peptide of SEQ ID NO: 4 (Glu-Leu-Ile-Glu-His-Gly-Gly-Gly-Arg-Pro-Ala-Asp: ELIEHGGGRPAD) were synthesized in the same manner as in Example <1-1-1>.

TABLE 1

| SEQ ID NO | Amino acid sequence | Analytical value (molecular weight analyzer) | |
|---|---|---|---|
| | | Analytical value | Theoretical value |
| 1 | Ac-YKSKKGGWTH | 1233.3 | 1233.4 |
| 2 | YISKKHAGKNW | 1478.8 | 1478.7 |
| 3 | KLKKTETQ | 975.1 | 975.1 |
| 4 | ELIEHGGGRPAD | 1250.9 | 1250.35 |

<1-2> Synthesis of Compounds of the Present Disclosure

To a peptide reactor, the peptidyl resin (1 mmol) and 10 ml of 1-methyl-2-pyrrolidone (NMP) were added, and 270 mg (2.0 equiv.) of 1-hydroxybenzotriazole (HOBt) and 759 mg (2.0 equiv.) of N,N,N',N'-tetramethyl-O-(1H-benzotriazol-1-yl)uronium hexafluorophosphate or O-(benzotriazol-1-yl)-N,N,N',N'-tetramethyl uronium hexafluorophosphate, and 277 mg (2.0 equiv.) of salicylic acid were added and allowed to react for 30 minutes. 388 mg (3 equiv.) of N,N-diisopropylethylamine (DIEA) was added and reacted at room temperature for 24 hours to 72 hours, and filtration was carried out to obtain a reacted peptidyl resin. The obtained resin was reacted with a cleavage solution at room temperature for 2 hours to remove the resin and the protecting group. Recrystallization was carried out using 10 ml (10 mmol) of diethyl ether to obtain a hybrid peptide.

Experimental Example 1. Test of Solubility of Compounds of the Present Disclosure The salicylic acid-peptide 1 compound (compound 1), the salicylic acid-peptide 2 compound (compound 2), the salicylic acid-peptide 3 compound (compound 3), and the salicylic acid-peptide 4 compound (compound 4) prepared in Example <1-2> and salicylic acid were dissolved in distilled water at a concentration of 10 mg/ml, respectively.

As a result, it was confirmed that salicylic acid as it is was hardly dissolved in water, whereas all of compound 1 to compound 4 of the present disclosure were completely dissolved in water (FIG. 1)

Experimental Example 2. Effects of Compounds of the Present Disclosure on Keratinocyte Growth To analyze growth factor-like efficacy and inhibitory efficacy of the compounds synthesized in Example <1-2>, a sulforhodamine B (SRB Sigma) colorimetric assay was performed using a HaCaT keratinocyte cell line (Korean Cell Line Bank) in accordance with a method of Rizzino, et al. (Cancer Res. 48:4266(1988))

HaCaT keratinocyte cell line was seeded in a 96-well plate at a density of 3,000 cells per well, and then cultured in Dulbecco's modified Eagle's medium (DMEM, Gibco, USA) containing 10% fetal bovine serum (FBS, Sigma) for 24 hours under conditions of 37° C. and 5% $CO_2$. The cultured cell line was detached from the bottom of the culture plate using a 1% trypsin solution, and only cell precipitate was collected by centrifugation. The cell precipitate was suspended in DMEM without FBS, and then cultured for 24 hours under conditions of 37° C. and 5% $CO_2$. 24 hours later, the medium was replaced by the same medium from which serum was completely removed. A blank sample in which the cell precipitate was dissolved sterile in 10% DMSO was prepared for standardization. Each of the compound 1 to the compound 4 (50 µM) of the present disclosure, salicylic acid (50 µM), and EGF (100 nM) as a positive control were treated. Incubation was carried out under the same conditions as above for 72 hours. After completing the incubation, each culture supernatant was removed and cells were fixed with ethanol and washed with phosphate buffer saline (PBS) three times. After removing the washing solution, the cells were treated with a colorimetric SRB solution, and then sufficiently washed with 1% acetic acid. The cells were observed under a microscope to examine living cells. Absorbance at UV 560 nm was measured to determine cell viability.

72 hours after treating keratinocytes with the compound of the present disclosure as above, changes in cell morphology were observed under a microscope. As a result, it was confirmed that the compounds of the present disclosure changed growth and morphology of keratinocytes (FIG. 2A). Further, salicylic acid used as the positive control inhibited growth of keratinocytes due to toxicity, whereas the compounds of the present disclosure greatly increased growth of keratinocytes (FIG. 2B).

Experimental Example 3. Antibacterial Effects of Compounds of the Present Disclosure Antibacterial effects of the compounds synthesized in Example <1-2> were examined using *Propionibacterium acnes*. To this end, *Propionibacterium acnes* was first cultured on an agar plate. Paper discs were soaked with each 200 mM of the compound 1 to the compound 4 synthesized in Example <1-2> and salicylic acid, and then the paper disc soaked with the sample was placed on the agar plate on which *Propionibacterium acnes* had been cultured, followed by incubation. 3 days later, the size of a clear zone with no microbial growth was measured to determine the antibacterial effect of each compound.

Figure 3A:
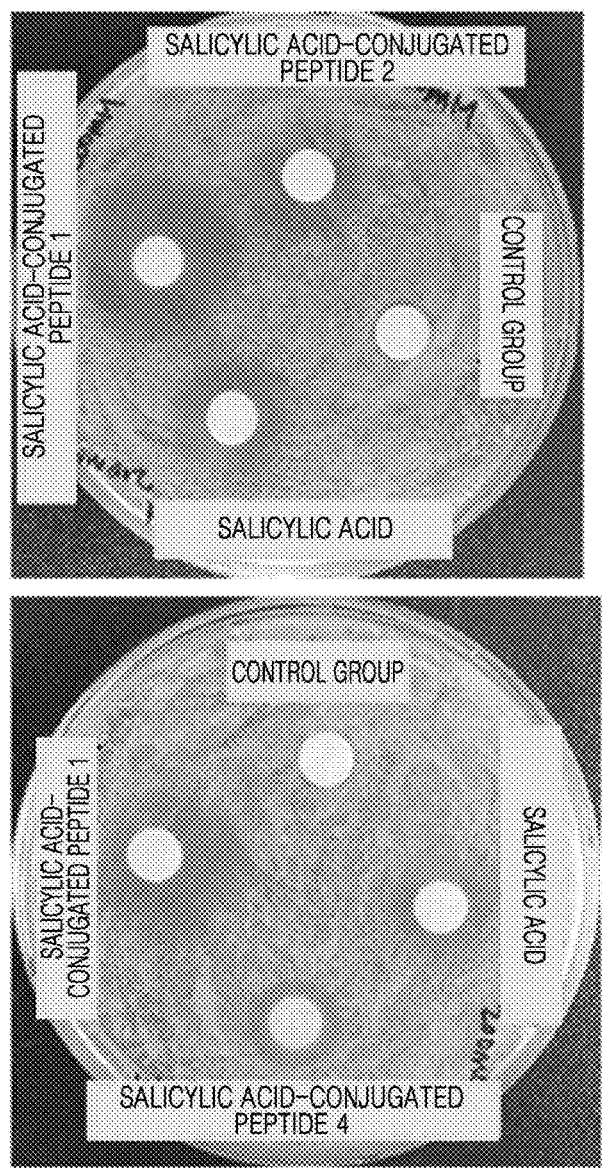
FIGS. 3A and 3B show images and graphs showing antibacterial activity against *Propionibacterium acnes* after treatment with the compounds of the present disclosure and salicylic acid, respectively.
Figure 3B:
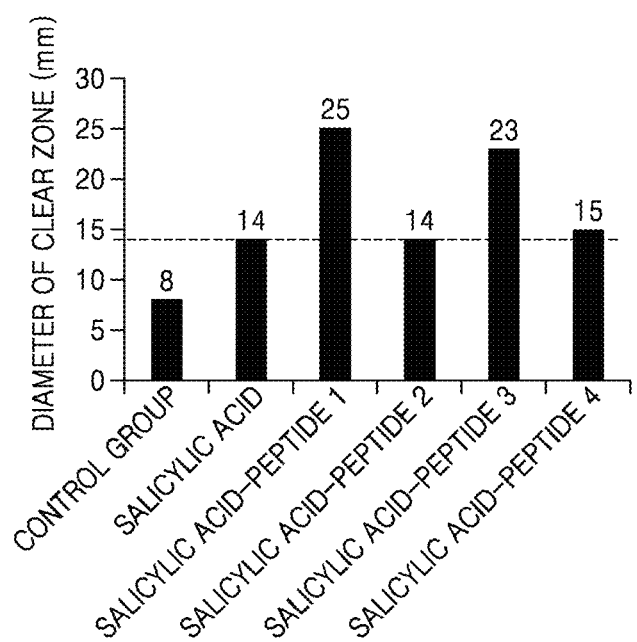
Figure 4A:
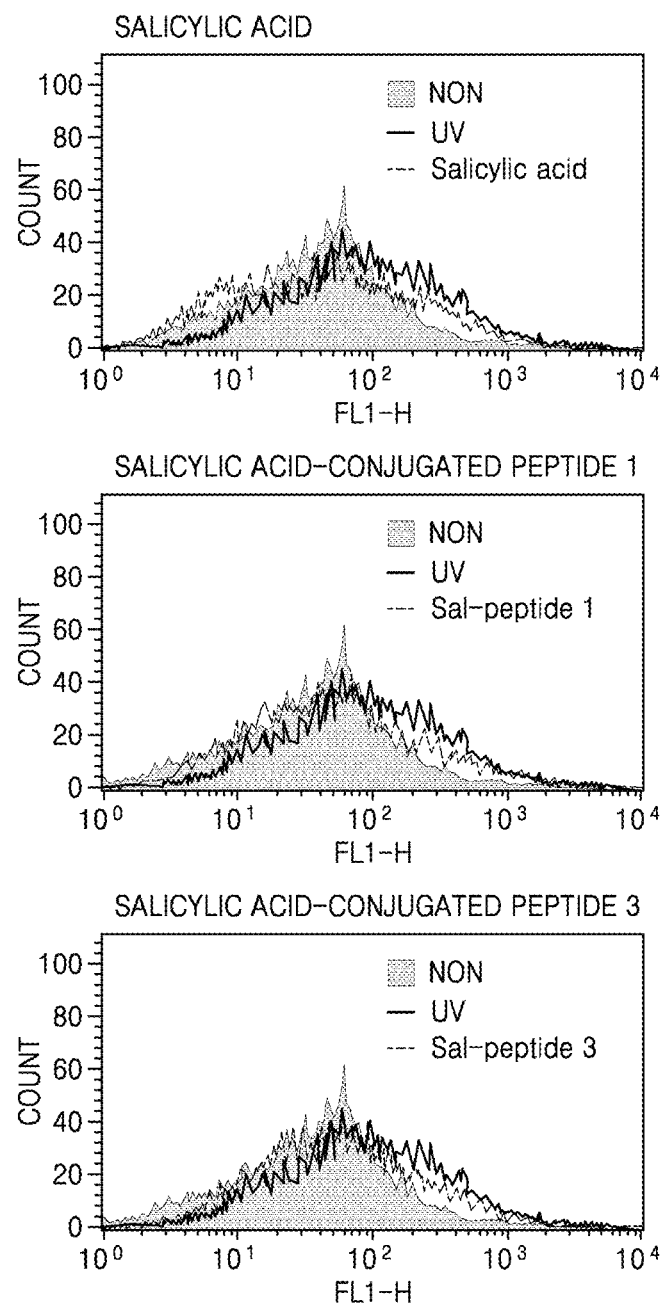
FIGS. 4A and 4B show results of fluorescence-activated cell sorting (FACS) and a graph showing relative levels of intracellular reactive oxygen species (ROS), respectively, indicating effects of the compounds of the present disclosure and salicylic acid on human hair dermal papilla cells (HHDPCs)
Figure 4B:
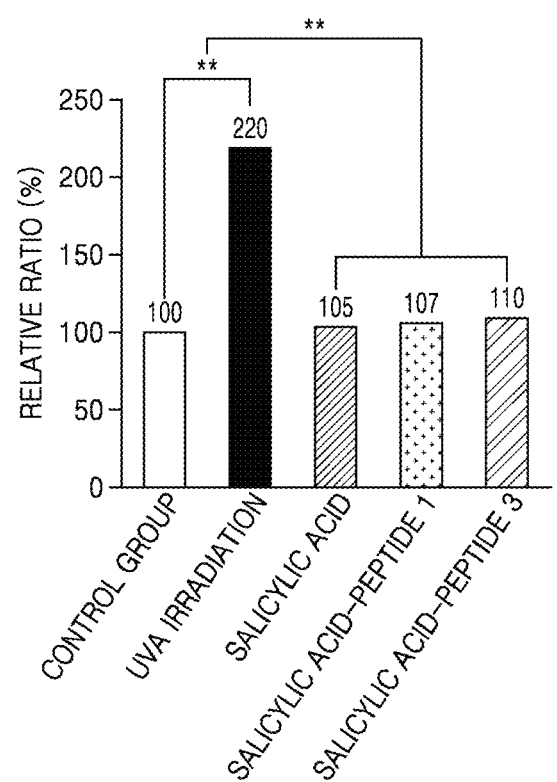
Figure 5A:
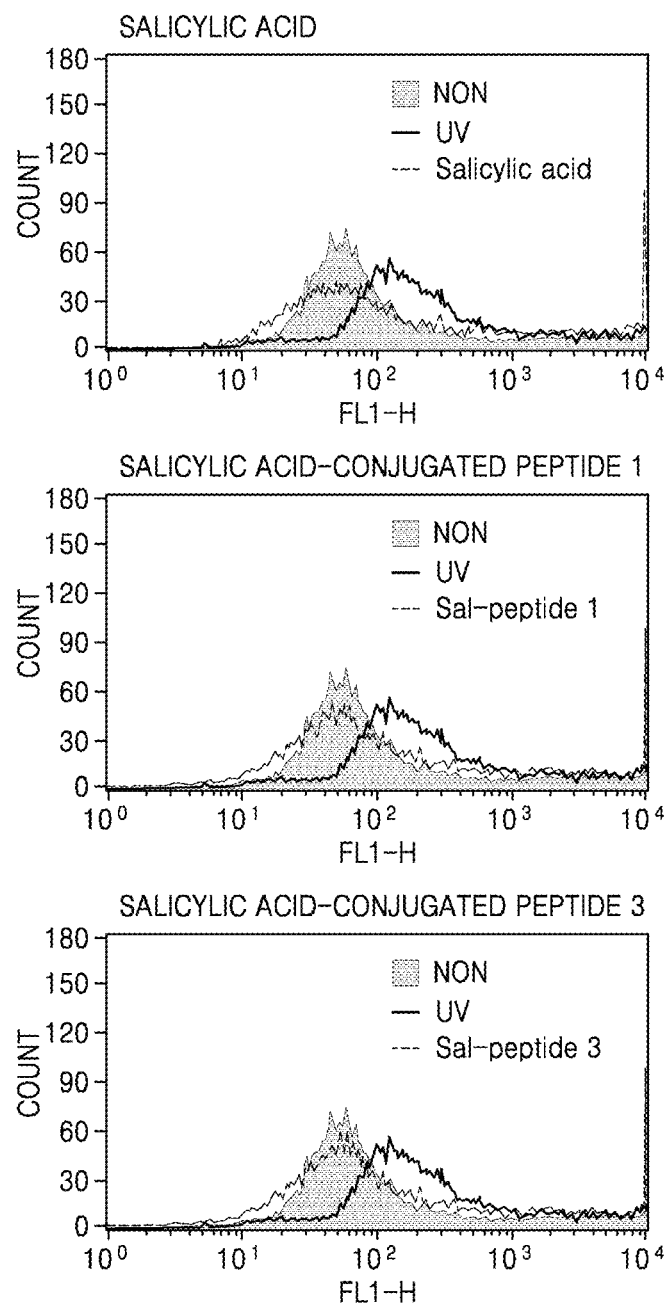
FIGS. 5A and 5B show results of FACS and a graph showing relative levels of intracellular ROS, respectively, indicating effects of the compounds of the present disclosure and salicylic acid on NIH3T3 fibroblasts.
Figure 5B:
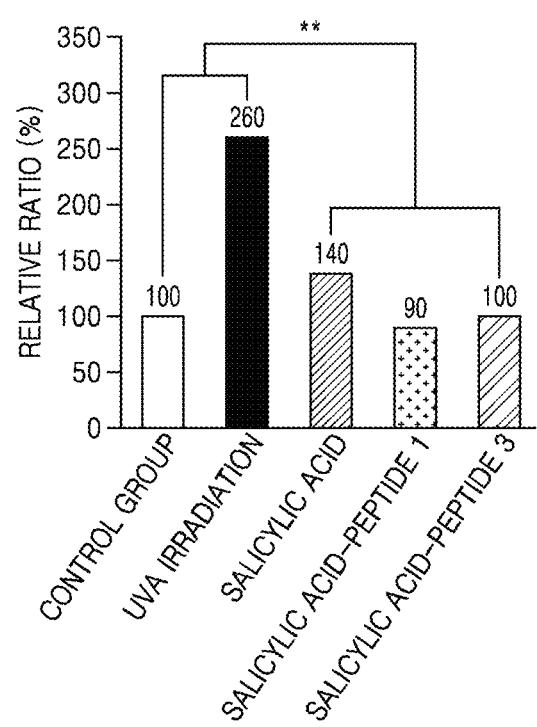
Figure 6A:
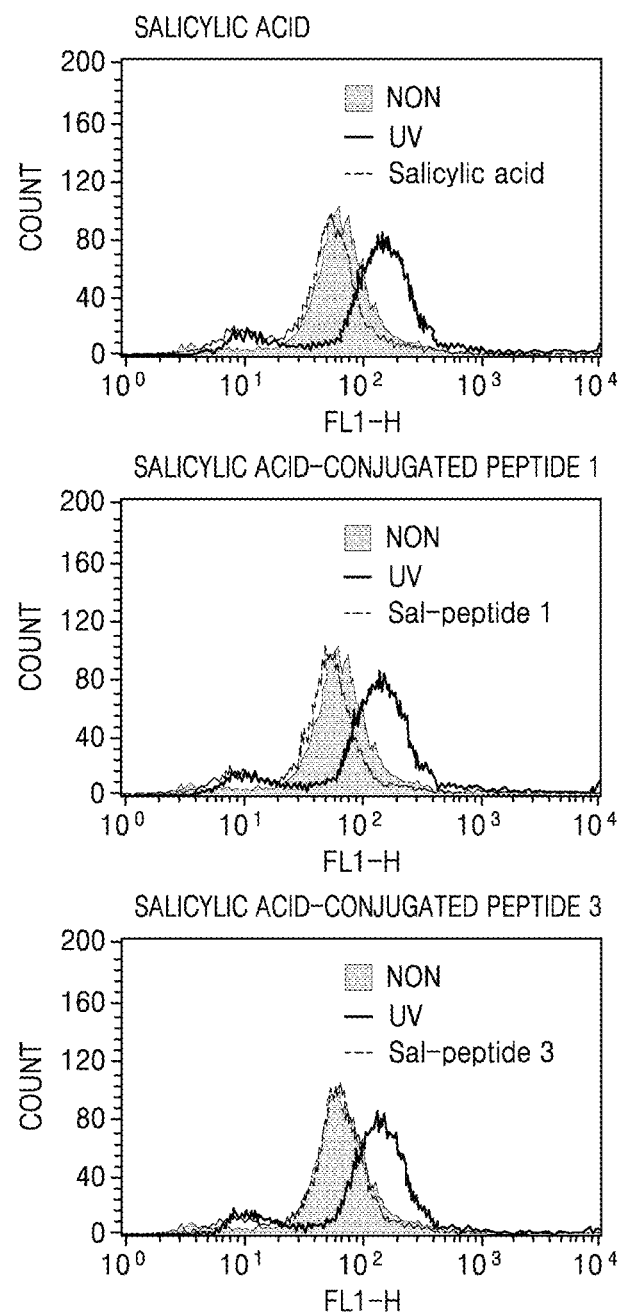
FIGS. 6A and 6B show results of FACS and a graph showing relative levels of intracellular ROS, respectively, indicating effects of the compounds of the present disclosure and salicylic acid on HaCaT keratinocytes.
Figure 6B:
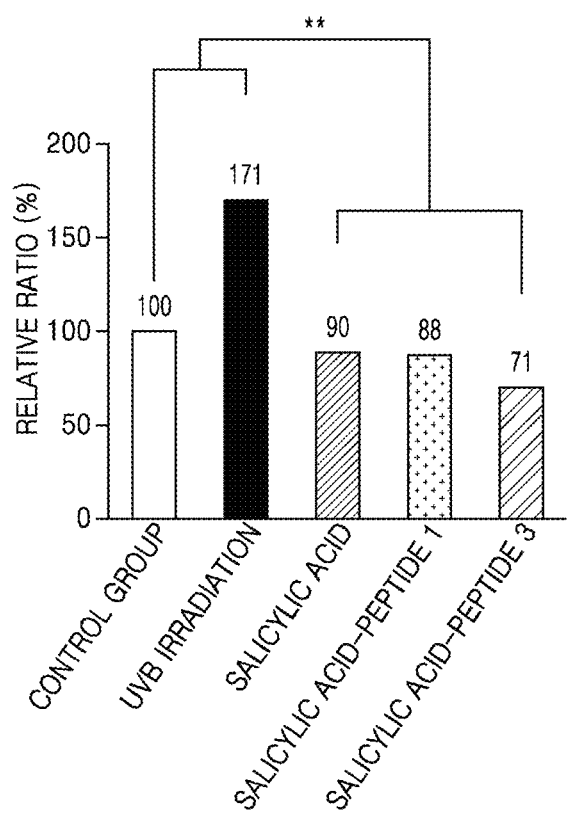

As a result, it was confirmed that the compounds of the present disclosure did not reduce the antibacterial effect of salicylic acid used as the positive control, and in particular, the compound 1 and the compound 3 showed remarkably increased antibacterial effects on *Propionibacterium acnes*, as compared with salicylic acid (FIGS. 3A and 3B).

Experimental Example 4. Antioxidant Effects of Compounds of the Present Disclosure Antioxidant effects of the compounds of the present disclosure were examined using human hair dermal papilla cell (HHDPC), NIH3T3 fibroblast, and HaCaT keratinocyte. To this end, the three kinds of the cell lines were cultured in a 96-well plate in the same manner as in Experimental Example 2, respectively and then treated with each 50 µM of the compound 1 and the compound 3 of the present disclosure and salicylic acid 1 hour before UV treatment. 50 mJ of UVB, 5 J of UVA, and 16 mJ of UVB were irradiated to HHDPC, NIH3T3 fibroblast, and HaCaT keratinocyte, respectively and DCFH-DA was treated thereto. The cells were incubated for 30 minutes, and then recovered. The cells were dispersed in PBS, and then FL1 values were measured using FACS, and used to examine changes in intracellular reactive oxygen species.

As a result, it was confirmed that the compounds of the present disclosure did not reduce the antioxidant effect of salicylic acid used as the positive control, and in particular, the levels of intracellular reactive oxygen species generated by UV treatment were the same as or much lower than those of salicylic acid (FIGS. 4A to 6B).

Experimental Example 5. Effect of Compounds of the Present Disclosure on Extracellular Matrix Expression Effects of the compounds of the present disclosure on extracellular matrix expression were examined using NIH3T3 fibroblast. To this end, NIH3T3 fibroblast was seeded in a 6-well plate at a density of 300,000 cells per well, and then incubated in a DMEM culture medium (Gibco, USA) containing 10% FBS for 24 hours under conditions of 37° C. and 5% $CO_2$. The cultured cell line was detached from the bottom of the culture plate using a 1% trypsin solution, and a cell precipitate was collected by centrifugation. The cell precipitate was suspended in DMEM without FBS, and then cultured for 24 hours under conditions of 37° C. and 5% $CO_2$. 24 hours later, the medium was replaced by the same medium from which serum was completely removed. A blank sample in which the cell precipitate was dissolved sterile in 10% DMSO was prepared for standardization. Each of the compound 1 and the compound 3 of the present disclosure, and salicylic acid as a positive control were treated at a concentration of 50 μM. Incubation was carried out under the same conditions as above for 72 hours. Thereafter, to examine collagen, elastin, and fibronectin expression by immunocytostaining, cells were fixed with 4% paraformaldehyde, permeated with 0.5% Triton X-100, and blocked with 3% BSA. The cells were treated with primary antibodies against respective collagen, elastin, and fibronectin at 1:100, and incubated at 4° C. overnight. The cells were treated with secondary antibodies at 1:500, and reacted at room temperature for 2 hours, and then nuclear staining and mounting were carried out using DAPI, followed by observation under a fluorescent microscope.

Meanwhile, RNA was isolated from the cells treated in the same manner as the above experiment, and then cDNA was synthesized using a cDNA synthesis kit (Intron, Korea). PCR premix (Intron, Korea) and primers for each of collagen, elastin, and fibronectin in Table 2 below were used to perform PCR. Thereafter, mRNA levels of collagen, elastin, and fibronectin were determined by 5% agarose gel electrophoresis.

TABLE 2

| Target | | | Primer sequence | | SEQ ID NO |
|---|---|---|---|---|---|
| Collagen | Forward | (5') | CACCCTCAAGAGCCTGAGTC | (3') | 5 |
| | Reverse | (5') | AGACGGCTGAGTAGGGAACA | (3') | 6 |
| Elastin | Forward | (5') | GGACCCCTGACTCGCGACCT | (3') | 7 |
| | Reverse | (5') | GGGGAGGTGGGACTGCCCAA | (3') | 8 |
| Fibro- | Forward | (5') | CCAGGAACCGAGTACACCAT | (3') | 9 |
| nectin | Reverse | (5') | ATACCCAGGTTGGGTGATGA | (3') | 10 |

Figure 7A:
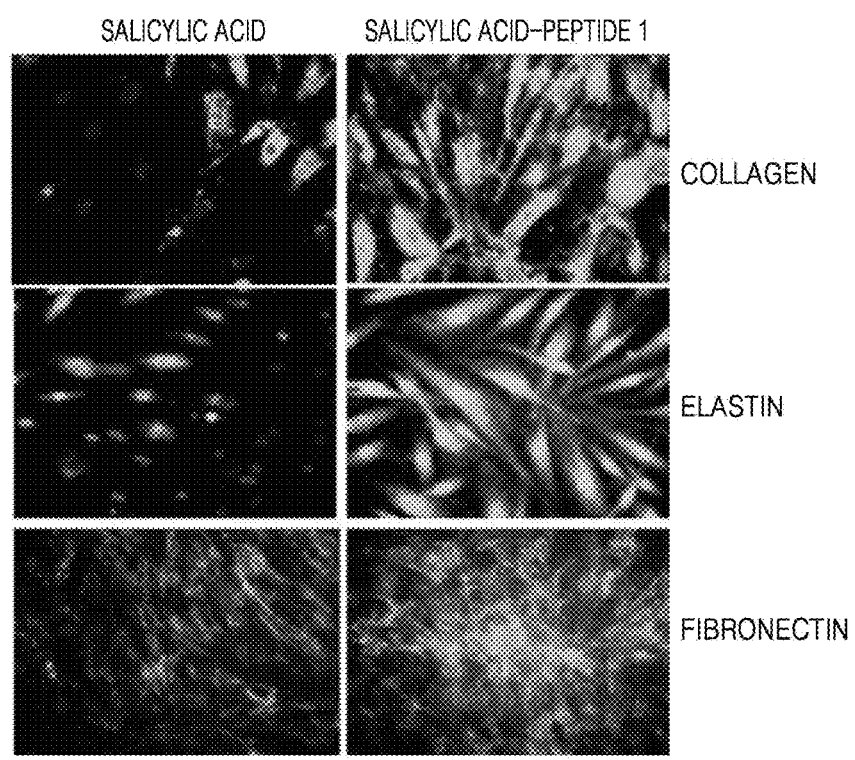
FIGS. 7A and 7B show results of immunohistochemical staining and RT-PCR, indicating effects of the compounds of the present disclosure and salicylic acid on extracellular matrix expression in HaCaT keratinocytes, respectively.
Figure 7B:
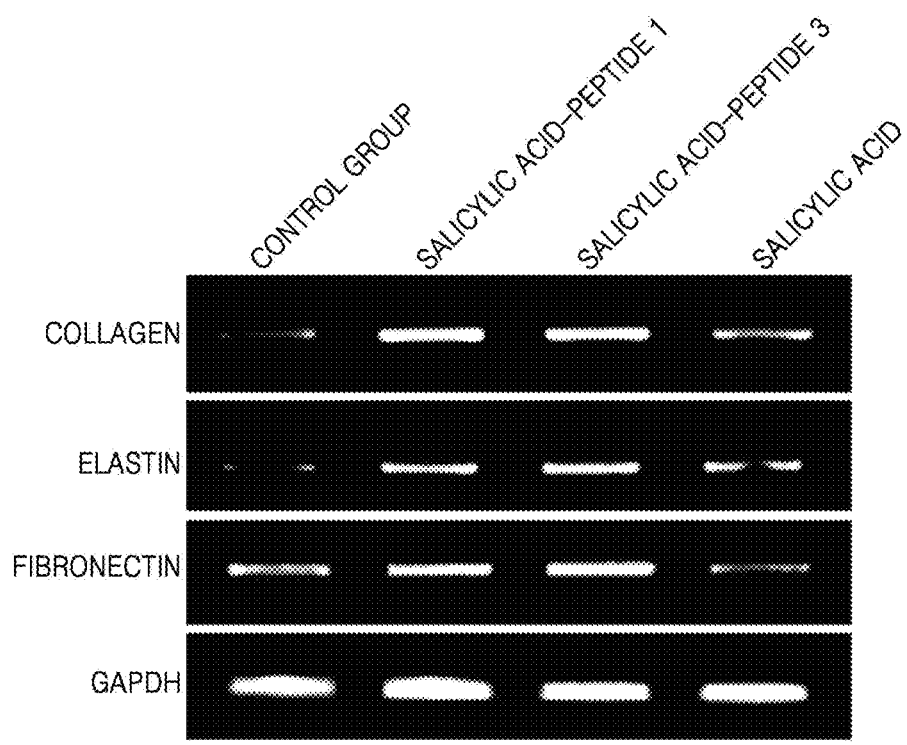

As a result, it was confirmed that the compound 1 and the compound 3 of the present disclosure remarkably increased protein and mRNA expression levels of collagen, elastin, and fibronectin which constitute extracellular matrix, as compared with salicylic acid used as the positive control (FIGS. 7A and 7B).

Experimental Example 6. Anti-Inflammatory Effects of Compounds of the Present Disclosure Anti-inflammatory effects of the compounds of the present disclosure were examined using *Propionibacterium acnes*. To this end, keratinocyte was seeded in a 6-well plate at a density of 300,000 cells per well, and then incubated in a DMEM culture medium (Gibco, USA) containing 10% FBS for 24 hours under conditions of 37° C. and 5% $CO_2$. After replacing the medium by a fresh medium, the cells were treated with 50 μg/ml of *Propionibacterium acnes*, and then the treated *Propionibacterium acnes* was treated with each 50 μM of the compound 1 and the compound 3 of the present disclosure and salicylic acid used as the positive control, followed by incubation for 24 hours under the same conditions as above. RNA was isolated from the cells, and cDNA was synthesized using a cDNA synthesis kit (Intron, Korea). PCR premix (Intron, Korea) and primers for each of TNF-α, IL-6, IL-1b, and COX-2 in Table 3 below were used to perform PCR. mRNA levels of TNF-α, IL-6, IL-1 b and COX-2 were determined by 5% agarose gel electrophoresis.

TABLE 3

| Target | | | Primer sequence | | SEQ ID NO |
|---|---|---|---|---|---|
| TNF-a | Forward | (5') | CGTCAGCCGATTRTGCTATCT | (3') | 11 |
| | Reverse | (5') | CGGACTCCGCAAAGTCTAAG | (3') | 12 |
| IL-6 | Forward | (5') | AAAGAGGCACTGCCAGAAAA | (3') | 13 |
| | Reverse | (5') | ATCTGAGGTGCCCATGCTAC | (3') | 14 |
| IL-1B | Forward | (5') | TTCGACACATGGGATAACGA | (3') | 15 |
| | Reverse | (5') | TCTHCAACACGCAGGACAG | (3') | 16 |
| COX-2 | Forward | (5') | ATCATTCACCAGGCAAATTGC | (3') | 17 |
| | Reverse | (5') | GGCTTCAGCATAAAGCGTTTG | (3') | 18 |

Figure 8:
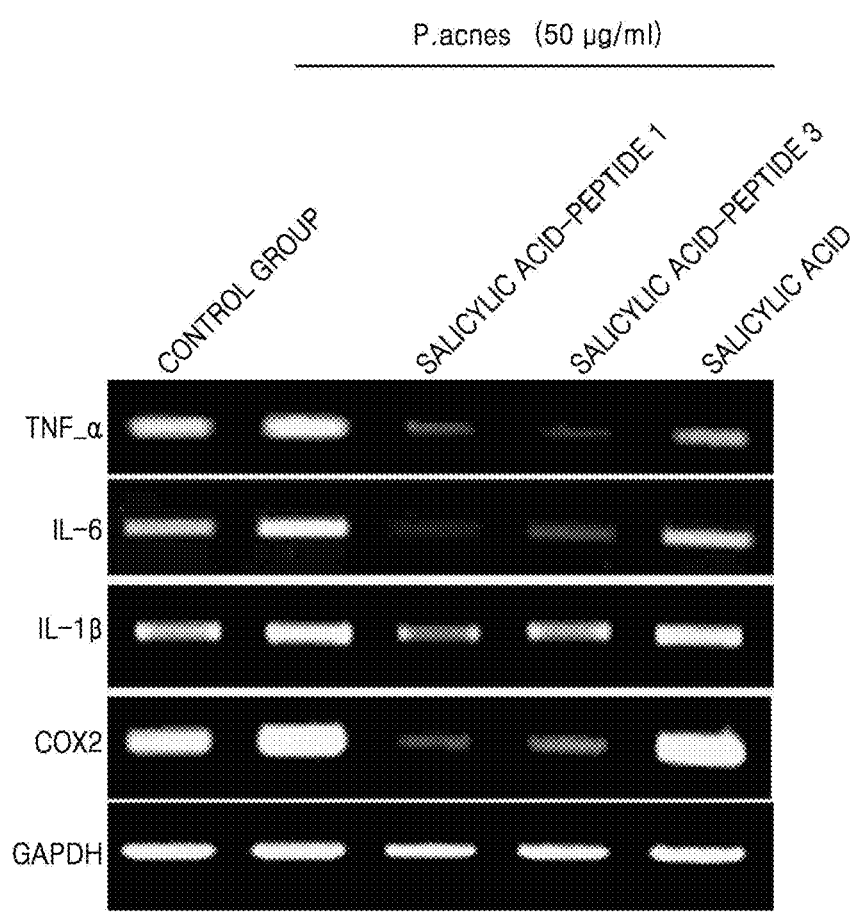
FIG. 8 shows an electrophoresis image showing effects of the compounds of the present disclosure and salicylic acid on *Propionibacterium acnes*-induced inflammatory cytokine expression in HaCaT keratinocytes.

As a result, it was confirmed that the compound 1 and the compound 3 of the present disclosure remarkably reduced expression of various inflammatory cytokines induced by *Propionibacterium acnes*, whereas salicylic acid used as the positive control hardly inhibited expression of the inflammatory cytokines (FIG. 8)

Formulation Example 1: Softener

A softener including the compound of the present disclosure prepared in Example <1-2> and consisting of the following composition was prepared according to a general method of preparing a toner.

TABLE 4

| Components | Content (% by weight) |
|---|---|
| Compound of the present disclosure | 2.5 |
| 1,3-Butylene glycol | 6 |
| Glycerin | 4 |
| PEG 1500 | 1 |
| Sodium hyaluronate | 1 |
| Polysorbate 20 | 0.5 |
| Ethanol | 8 |
| Preservative, Pigment | Proper amount |
| Benzophenone-9 | 0.05 |
| Fragrance | Trace amount |
| Purified water | Residual amount |
| Total | 100 |

Formulation Example 2. Nutrient Cream

A nutrient cream including the compound of the present disclosure prepared in Example <1-2> and consisting of the following composition was prepared according to a general method of preparing a nutrient cream.

TABLE 5

| Components | Content (% by weight) |
|---|---|
| Compound of the present disclosure | 2.5 |
| Meadowfoam oil | 3 |
| Cetearyl alcohol | 1.5 |
| Stearic acid | 1.5 |
| Glyceryl stearate | 1.5 |
| Liquid paraffin | 10 |
| Wax | 2 |
| Polysorbate 60 | 0.6 |
| Sorbitan sesquiolate | 2.5 |
| Squalane | 3 |
| 1,3-Butylene glycol | 3 |
| Glycerin | 5 |
| Triethanolamine | 0.5 |
| Tocopheryl acetate | 0.5 |
| Preservative, Pigment | Proper amount |
| Fragrance | Proper amount |
| Purified water | Residual amount |
| Total | 100 |

Formulation Example 3. Nourishing Toner

A nourishing toner including the compound of the present disclosure prepared in Example <1-2> and consisting of the following composition was prepared according to a general method of preparing a toner.

TABLE 6

| Components | Content (% by weight) |
|---|---|
| Compound of the present disclosure | 2.5 |
| 1,3-Butylene glycol | 4 |
| Glycerin | 4 |
| Cetearyl alcohol | 0.8 |
| Glyceryl stearate | 1 |
| Triethanolamine | 0.13 |
| Tocopheryl acetate | 0.3 |
| Liquid paraffin | 5 |
| Squalane | 3 |
| Makadamianut oil | 2 |
| Polysorbate 60 | 1.5 |
| Sorbitan sesquiolate | 0.5 |
| Carboxyvinyl polymer | 1 |
| Preservative, Pigment | Proper amount |
| Fragrance | Proper amount |
| Purified water | Residual amount |
| Total | 100 |

Formulation Example 4. Essence

An essence including the compound of the present disclosure prepared in Example <1-2> and consisting of the following composition was prepared according to a general method of preparing an essence.

TABLE 7

| Components | Content (% by weight) |
|---|---|
| Compound of the present disclosure | 2.5 |
| Glycerin | 10 |

TABLE 7-continued

| Components | Content (% by weight) |
|---|---|
| 1,3-Butylene glycol | 5 |
| PEG 1500 | 2 |
| Allantoin | 0.1 |
| DL-Panthenol | 0.3 |
| EDTA-2Na | 0.02 |
| Hydroxyethyl cellulose | 0.1 |
| Sodium hyaluronate | 8 |
| Carboxyvinyl polymer | 0.2 |
| Triethanolamine | 0.18 |
| Octyldodeceth-16 | 0.4 |
| Ethanol | 6 |
| Fragrance, Preservative, Pigment | Proper amount |
| Purified water | Residual amount |
| Total | 100 |

Formulation Example 5. Hair Serum

A hair serum including the compound of the present disclosure prepared in Example <1-2> and consisting of the following composition was prepared according to a general method of preparing a hair serum.

TABLE 8

| Components | Content (% by weight) |
|---|---|
| Compound of the present disclosure | 1 |
| Glycerin | 10 |
| 1,3-Butylene glycol | 5 |
| PEG 1500 | 2 |
| Allantoin | 0.1 |
| DL-Panthenol | 0.3 |
| EDTA-2Na | 0.02 |
| Hydroxyethyl cellulose | 0.1 |
| Sodium hyaluronate | 8 |
| Carboxyvinyl polymer | 0.2 |
| Triethanolamine | 0.18 |
| Octyldodeceth-16 | 0.4 |
| Ethanol | 6 |
| Fragrance, Preservative, Pigment | Proper amount |
| Purified water | Residual amount |
| Total | 100 |

Formulation Example 6. Hair Toner

A hair serum including the compound of the present disclosure prepared in Example <1-2> and consisting of the following composition was prepared according to a general method of preparing a hair serum.

TABLE 9

| Components | Content (% by weight) |
|---|---|
| Compound of the present disclosure | 1 |
| Glycerin | 2 |
| 1,3-Butylene glycol | 2 |
| PEG 1500 | 2 |
| Allantoin | 0.1 |
| DL-Panthenol | 0.3 |

TABLE 9-continued

| Components | Content (% by weight) |
|---|---|
| EDTA-2Na | 0.02 |
| Sodium hyaluronate | 8 |
| Carboxyvinyl polymer | 0.2 |
| Triethanolamine | 0.18 |
| Ethanol | 10 |
| Fragrance, Preservative, Pigment | Proper amount |
| Purified water | Residual amount |
| Total | 100 |

The invention claimed is:

1. A compound having a structure in which salicylic acid is linked to a water-soluble peptide via a covalent bond, wherein the peptide consists of 8 to 12 amino acids, wherein, in the peptide, the proportion of amino acids having hydrophilic side chains is 50% or more, and the number of amino acids having hydrophobic side chains is 1 or more.

2. The compound of claim 1, wherein, in the water-soluble peptide, the proportion of amino acids having hydrophilic side chains is 70% or more.

3. The compound of claim 2, wherein, in the water-soluble peptide, the proportion of amino acids having hydrophilic side chains is 90% or more.

4. The compound of claim 1, wherein the amino acids having hydrophilic side chains are selected from the group consisting of arginine (Arg), histidine (His), lysine (Lys), aspartic acid (Asp), glutamic acid (Glu), serine (Ser), threonine (Thr), asparagine (Asn), glutamine (Gln), cysteine (Cys), selenocysteine (Sec), glycine (Gly), and proline (Pro).

5. The compound of claim 1, wherein, in the water-soluble peptide, the number of amino acids having hydrophobic side chains is 5 or less.

6. The compound of claim 5, wherein, in the water-soluble peptide, the number of amino acids having hydrophobic side chains is 3 or less.

7. The compound of claim 1, wherein the amino acids having hydrophobic side chains are selected from the group consisting of alanine (Ala), valine (Val), isoleucine (Ile), leucine (Leu), methionine (Met), phenylalanine (Phe), tyrosine (Tyr), and tryptophan (Trp).

8. The compound of claim 1, wherein the peptide is selected from the group consisting of the amino acid sequences of SEQ ID NO: 1 to SEQ ID NO: 4.

9. A pharmaceutical composition comprising the compound of claim 1.

10. A cosmetic composition comprising the compound of claim 1.

11. The cosmetic composition of claim 10, wherein the cosmetic composition has a formulation selected from the group consisting of a softener, a nourishing toner, a nutrient cream, a massage cream, an essence, an eye cream, a cleansing cream, a cleansing foam, a cleansing water, a pack, a spray, a powder, a hair tonic, a hair cream, a hair lotion, a hair shampoo, a hair rinse, a hair conditioner, a hair spray, a hair aerosol, a pomade, a sol gel, an emulsion, an oil, a wax, and an aerosol.

12. A method for treating an infection of *Propionibacterium acnes* in a subject, the method comprising administering the compound of claim 1 to the skin of a subject.

13. A method of improvement of a skin condition, the method comprising administering the compound of claim 1 to the skin of a subject, wherein the skin condition is selected from the group consisting of wrinkle improvement, skin elasticity improvement, skin moisturizing improvement, wound repair, and skin regeneration.

* * * * *

SEQUENCE LISTING

```
<160> NUMBER OF SEQ ID NOS: 18

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Tyr Lys Ser Lys Lys Gly Gly Trp Thr His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Tyr Ile Ser Lys Lys His Ala Gly Lys Asn Trp Phe
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Lys Leu Lys Lys Thr Glu Thr Gln
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic Construct

<400> SEQUENCE: 4

Glu Leu Ile Glu His Gly Gly Gly Arg Pro Ala Asp
1               5                   10

<210> SEQ ID NO 5
<211> LENGTH: 20
<212> TYPE: DNA
<213> ORGANISM: Artificial Sequence
<220> FEATURE:
<223> OTHER INFORMATION: Synthetic Costruct

<400> SEQUENCE: 5
caccctcaag agcctgagtc                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
agacggctga gtagggaaca                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ggacccctga ctcgcgacct                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
ggggaggtgg gactgcccaa                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ccaggaaccg agtacaccat                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
atacccaggt tgggtgatga                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
cgtcagccga ttrtgctatc t                                                 21

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 12
cggactccgc aaagtctaag                                                     20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
aaagaggcac tgccagaaaa                                                     20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
atctgaggtg cccatgctac                                                     20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
ttcgacacat gggataacga                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tctttcaaca cgcaggacag                                                     20

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
atcattcacc aggcaaattg c                                                   21

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
ggcttcagca taaagcgttt g                                                   21
```